United States Patent [19]

Scott et al.

[11] Patent Number: 5,332,738
[45] Date of Patent: Jul. 26, 1994

[54] IMIDAZOLIDINE ANTIPSYCHOTIC AGENTS

[75] Inventors: Malcolm K. Scott; Allen B. Reitz, both of Lansdale, Pa.

[73] Assignee: NcNeilab, Inc., Spring House, Pa.

[21] Appl. No.: 943,663

[22] Filed: Sep. 11, 1992

[51] Int. Cl.$^5$ ............... A61K 31/495; A61K 31/445; C07D 403/10; C07D 401/10
[52] U.S. Cl. .................... 514/252; 544/373; 546/208
[58] Field of Search ............ 544/373; 514/252; A61K 31/495

[56] References Cited

U.S. PATENT DOCUMENTS 4,891,375 1/1990 Lowe III ................... 544/370

Primary Examiner—Cecilia Tsang
Attorney, Agent, or Firm—Ralph R. Palo

[57] ABSTRACT

Compounds of the general formula I

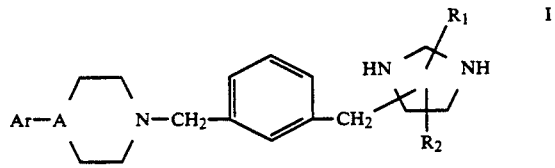

are disclosed as novel antipsychotic agents. Pharmaceutical compositions and methods of treating convulsions employing such compounds of formula I.

16 Claims, No Drawings

IMIDAZOLIDINE ANTIPSYCHOTIC AGENTS

BACKGROUND OF THE INVENTION

Antipsychotic drugs are known to alleviate the symptoms of mental illnesses such as schizophrenia. Examples of such drugs include phenothiazine derivatives such as promazine, chlorpromazine, fluphenazine, thioridazine and promethazine, thioxanthenes such as chlorprothixene, butyrophenones such as haloperidol and clozapine. While these agents may be effective in treating schizophrenia, virtually all except clozapine produce extrapyramidal side effects, such as facial tics or tardive dyskinesia. Since antipsychotics may be administered for years or decades to a patient, such pronounced side effects may complicate recovery and further isolate the individual from society.

The present invention describes novel compounds that combine antipsychotic effects with minimal or reduced side effects such as extrapyramidal symptomology relative to some of the compounds known in the art.

SUMMARY OF THE INVENTION

Compounds of the general formula I:

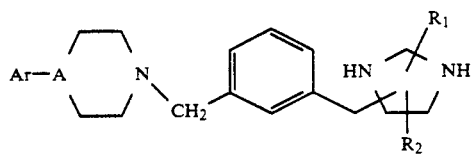

wherein Ar, A, $R_1$ and $R_2$ are as defined hereinafter, are potent antipsychotic agents useful in the treatment of psychotic conditions such as schizophrenia in mammals including humans. The compounds of the present invention may also be useful in the treatment of other disorders of the central nervous system such as anxiety and aggression. The present invention is also directed to pharmaceutical compositions containing the compounds of formula I and methods of treating psychotic conditions employing such compounds.

DETAILED DESCRIPTION OF THE INVENTION

The present invention is directed to compounds of the general formula I:

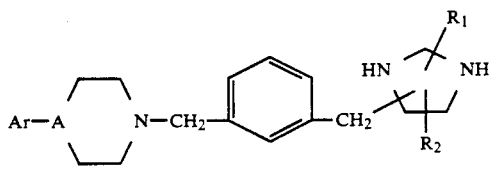

wherein

A is N or CH, but preferably N.

Ar is aryl or substituted aryl. The aryl group may be independently substituted with one or more of $C_1$-$C_8$ alkyl, $C_3$-$C_{10}$ cycloalkyl, $C_1$-$C_8$ hydroxyalkyl, $C_1$-$C_8$ alkoxy, aryloxy, hydroxyl, trifluoromethyl, trifluoromethoxy, cyano, $C_1$-$C_8$ alkylthio, halogen, nitro, $C_1$-$C_8$ haloalkyl, amino or $C_1$14 $C_8$ mono-or dialkylamino. More preferably, Ar is substituted phenyl. The more preferred substituents are selected from any of $C_1$-$C_8$ alkoxy. Most preferably, the substituent is isopropoxy. The preferred site of substitution is the 2-position on the phenyl ring.

$R_1$ and $R_2$ may be the same or different and are selected from either of =O (oxo group) or =S (thioxo group). $R_1$ and $R_2$ are always separated in their sites of substitution on the ring by a ring N atom, which thus creates the hydantoin or thiohydantoin ring systems. More preferably, at least one of $R_1$ and $R_2$ is O.

The imidazolidine ring may be attached to the remainder of the molecule at any ring atom.

As used herein, unless otherwise noted, alkyl and alkoxy whether used alone or part of a substituent group, include straight and branched chains. For example, alkyl radicals include methyl, ethyl, propyl, isopropyl, n-butyl, isobutyl, sec-butyl, t-butyl, n-pentyl, 2-pentyl, 2-methylbutyl, neopentyl, n-hexyl, 2-hexyl, 2-methylpentyl. Alkoxy radicals are oxygen ethers formed from the previously described straight or branched chain alkyl groups. Of course, if the alkyl or alkoxy substituent is branched there must be at least 3 carbons.

The term "aryl" as used herein alone or in combination with other terms indicates aromatic hydrocarbon groups such as phenyl or naphthyl. With reference to substituents, the term independently means that when more than one of such substituent is possible such substituents may be the same or different from each other.

Examples of particularly preferred compounds include:

3-[[3-[[1-[2-(1-Methylethoxy)phenyl]-4-piperazinyl]methyl]phenyl]methyl]-2,4-imidazolidinedione (CP #1)

1-[[3-[[1-[2-(1-Methylethoxy)phenyl]-4-piperazinyl]methyl]phenyl]methyl]-2,4-imidazolidinedione (CP #2)

3-[[3-[[1-[2-(Methylethoxy)phenyl]-4-piperazinyl]methyl]phenyl]methyl]imidazolidine-4-one-2-thione (CP #3)

5-[[3-[[1 -[2-(1-Methylethoxy)phenyl]-4-piperazinyl]methyl]phenyl]methyl]-2,4-imidazolidinedione (CP #4)

Within the scope of the invention are compounds of the invention in the form of hydrates and other solvate forms.

Representative salts of the compounds of formula I which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic p-toluenesulfonic, cyclohexanesulfamic, salicyclic, p-aminosalicyclic, 2-phenoxybenzoic, 2-acetoxybenzoic or a salt made with saccharin. Such salts can be made by reacting the free base of formula I with the acid and recovering the salt.

The compounds of formula I may be prepared according to the following reaction scheme.

REACTION SCHEME 1

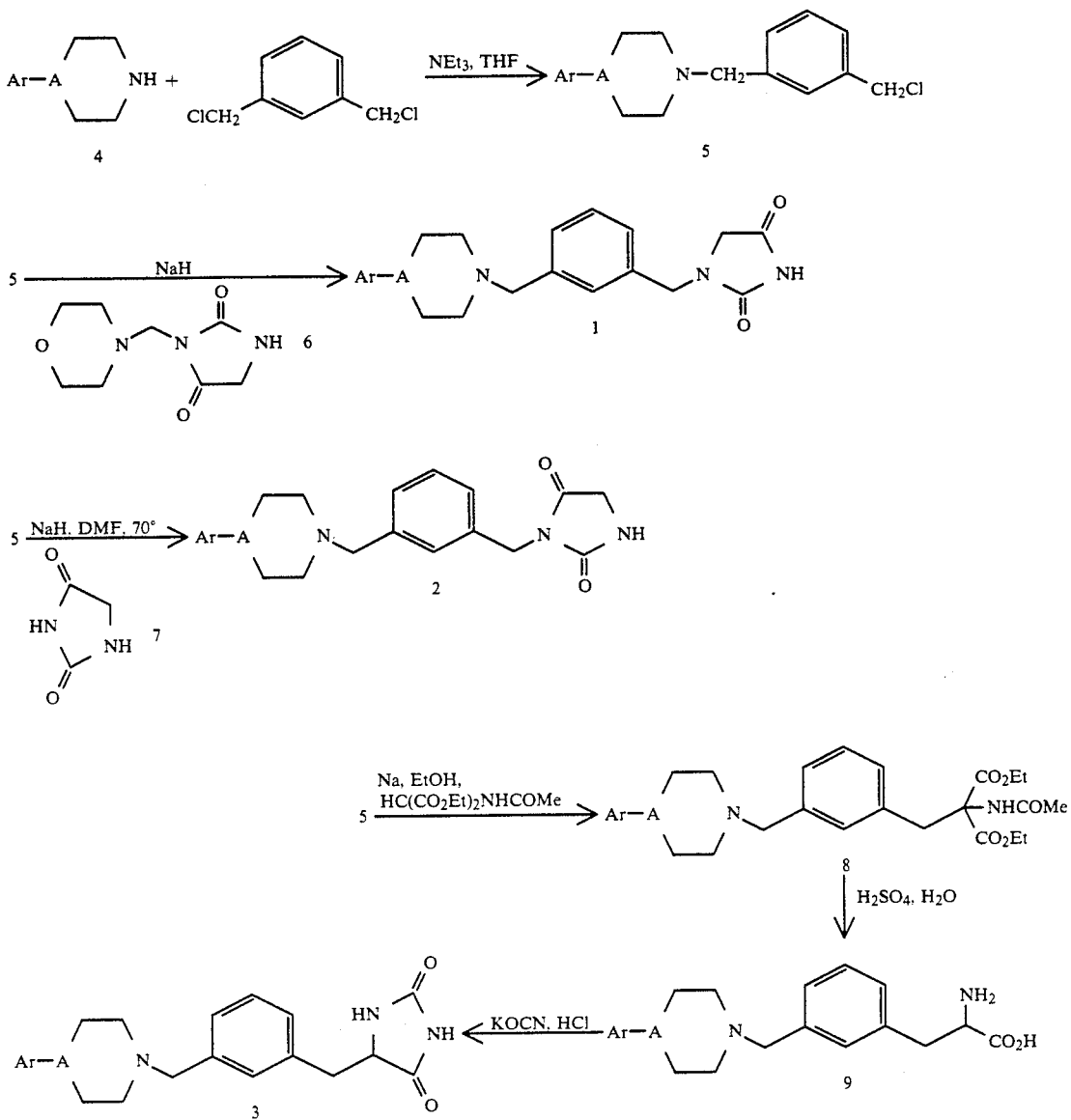

In the Reaction Scheme 1, compounds of formula 1-3 are prepared starting from a benzylchloride of formula 5. In the preparation of 1, compound 5 is reacted with a hydantoin of formula 6 in the presence of a base such as NaH in a suitable solvent such as DMF or THF. HOAc (acetic acid) is used then to cleave the protecting morpholino methyl group. Compound 6 is made as described by Orazi and Corral, *Tetrahedron*, 1961, 15, 93-99. Benzylchlorides 5 are obtained from the reaction of piperidines or piperazines 4 with α,α'-dichloro-m-xylene in the presence of an amine base such as triethylamine and in a solvent such as THF. The compounds of formula 4 are either commercially available or may be made by methods known in the art. See, for example, G. E. Martin et al., *J. Med. Chem.*, 1989, 32, 1051.

Compounds 2 are obtained in a similar fashion by the treatment of compounds of formula 5 with hydantoin 7 in the presence of a base such as NaH in a suitable solvent such as DMF or THF.

Hydantoins of formula 3 are prepared by the cyclization of amino acids of formula 9 using KOCN in the presence of a suitable acid such as HCl, in a suitable solvent such as water. Amino acids of formula 9 are obtained from the reaction of benzylchlorides of formula 5 with diethyl acetamidomalonate, which has been treated with sodium ethoxide, in the presence of a solvent such as ethyl alcohol and hydrolysis and decarboxylation of the resulting 1,3-propanedioate 8 in the presence of an acid such as $H_2SO_4$ and a solvent such as water.

REACTION SCHEME 2

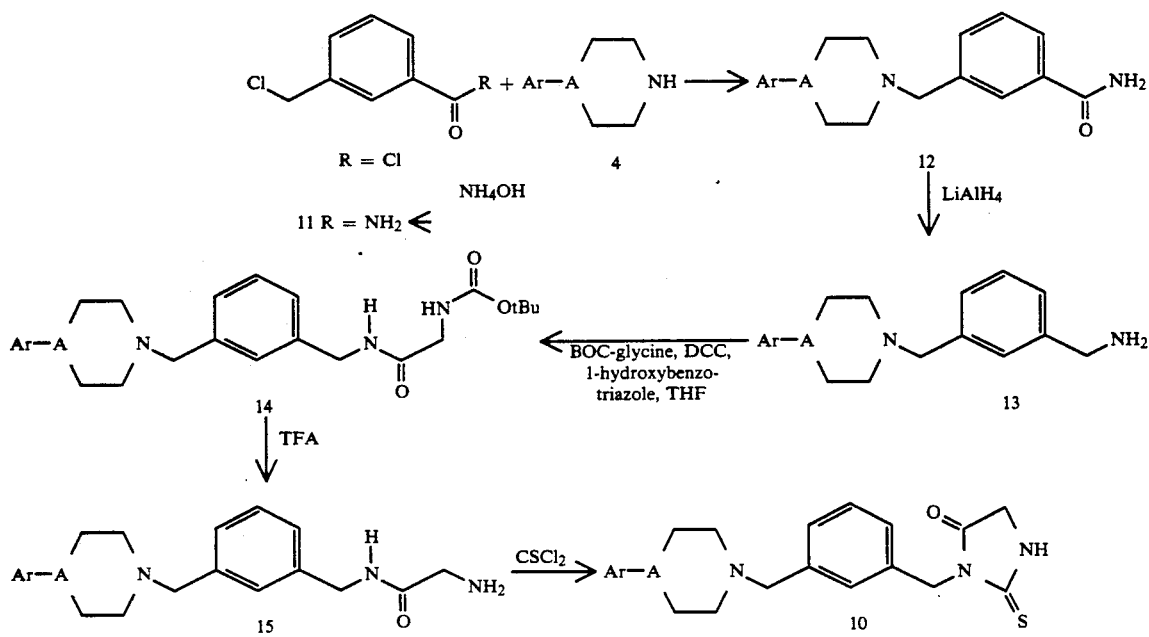

In Reaction Scheme 2, compounds of formula 10 are obtained by treating an amide of formula 15 with thiophosgene in the presence of triethylamine or other suitable base, using a suitable solvent such as $CH_2Cl_2$. Compounds of formula 15 are prepared by first treating 3-chloromethylbenzamide, obtained from commercially available 3-chloromethylbenzoyl chloride and $NH_4OH$, with a compound of formula 4 in a suitable solvent such as THF using a suitable base such as triethylamine as an acid scavenger, to give benzamides of formula 12, which are then reduced to the corresponding amines of formula 13 with a reducing agent such as lithium aluminum hydride in a solvent such as dioxane. Conversion of amines of formula 13 to amides of formula 14, using tert-butyloxycarbonylglycine (BOC-glycine) and dicyclohexylcarbodiimide (DCC) in the presence of 1-hydroxybenzotriazole with THF as solvent, followed by removal of the BOC group with trifluoroacetic acid (TFA) affords compounds of formula 15.

The antipsychotic activity of the compounds of the invention may be determined by the Block of Conditioned Avoidance Responding (Rat) test (CAR), references being Cook, L. and E. Weidley in *Ann. N. Y. Acad. Sci.*, 1957, 6, 740–752, and Davidson, A. B. and E. Weidley in *Life Sci.*, 1976, 18, 1279–1284. This test was performed for compounds disclosed in this invention, and the data are listed in Table 1.

Block of Conditioned Avoidance Responding (Rat)

Apparatus: Rat operant chambers, housed within sound attenuated booths, both from Capden Instruments Ltd., were used in this test. The test chamber (8" H×90⅜" W×9" D) is constructed of aluminum and plexiglass with floor grid bars of stainless-steel (⅛" O.D.) spaced 9/16" apart. A stainless-steel operation level 1½" wide projects ¾" into the chamber and is positioned 2-2/8" above the grid floor. The shock stimulus is delivered via the grid floor by a Coulbourn Instruments solid state module. The parameters of the test and the collection of data are controlled automatically.

Training: Male, Fischer 344 rats obtained from Charles River (Kingston, N.Y.) weighing more than 200 g, are individually housed with chow and water provided ad libitum. The rats are trained for two weeks to approach criterion levels in the avoidance test (90% avoidance rate). One-hour training sessions are run at about the same time each day for four or five days a week. The training session consists of 120 trials, with the conditioned stimuli presented every 30 sec. A trial begins with presentation of the conditioned stimuli (a light and a tone). If the rat responds by depressing the operant lever during the 15-second presentation of the conditioned stimuli, the trial is terminated and the animal is credited with a CAR. Failure to respond during the conditioned stimuli causes the presentation of the unconditioned stimulus (UCS), a 0.7 mA shock which is accompanied by a light and tone for five seconds. If the rat depressed the lever within the ten-second period, the shock and trial are terminated and an escape response recorded. If the rat fails to depress the lever during the UCS (shock), the trial is terminated after ten seconds of shock and the absence of a response is scored as a failure to escape. Intertrial level presses have no effect. If a rat performs at the 90% CAR level for two weeks, it is then run twice a week on the test schedule (see below) until baseline performance stabilized. Before any drug is administered, two weeks of CAR at a rate of 90% or better is required.

Determination of $ED_{50}$ Values

Trained rats are run in a one-hour session on two consecutive days at the same time and in the same test chamber each day. The sessions consist of 60 trials, one every minute. The conditioned stimuli are presented for 15 sec (maximum) and the unconditioned stimuli five sec (maximum). On Day 1, a vehicle solution is administered to the rats at a time preceding the trial run corresponding to the pretreatment time for the test compound. The route of administration and the volume of vehicle are also matched to that of the test compound.

Only animals that exhibited greater than 90% CAR on Day 1 are given the test compound on Day 2.

Statistical Computations: $ED_{50}$ values (that dose required to reduce the mean number of CARS to 50% of the control mean) are determined in the following manner. The percent change in CAR on the drug treatment day compared to vehicle pretreatment day is the key measure. The percent change (% change)in CAR is determined using the following formula:

% change CAR=((Day 2% CAR/Day 1% CAR)×100)−100

A negative number indicates a blockade of CAR, whereas a positive number would indicate increased CAR. The test results are reported as the mean % change for the group of rats. A reading of −20% is generally taken to represent a minimum value for a compound to be designated as active at a given dose in the CAR test. Failure to escape was calculated for each animal as follows:

% Failures=# of Failures to Escape/# of trials

The % failures, viz., loss of escape, is also reported as a group mean. Failures to escape are monitored closely and a session is terminated if ten failures occurred. $ED_{50}$ values and 95% confidence limits are calculated using linear regression analysis. The results of the CAR tests are shown in Table 1.

Receptor Binding Assay

The dopamine $D_2$ binding activity of compounds was determined using a $P_2$ fraction (synaptosomal membranes) prepared from male, Wistar rats. The $D_2$ assay employed a $P_2$ fraction from the striatum, the ligand $^3$H-spiperone at a concentration of 0.05 nM, and 1 mM haloperidol as a blank determinant. Incubation was in 3 mM potassium phosphate buffer for 45 min at 37° C. Under these conditions, specific binding constituted 75% of total binding, and the $K_I$ values for some known drugs were: 0.37 nM for haloperidol and 82 nM for clozapine.

The data from this assay were analyzed by calculating the percent inhibition of the binding of the tritiated ligands by given concentrations of the test compound. $K_I$ values, where given, were obtained from the logit analysis of concentration-inhibition curves. A value of 1000 or less is generally taken to represent the value for a compound to be designated as active in this screen. If a compound is active in this screen, but not in the CAR screen, it is still considered an active antipsychotic agent because the CAR screen negative result may be due to site delivery problems which may be solved by a suitable delivery mechanism.

TABLE 1

| CP # | % inhibition Car, 5 mpk, ip | % escape loss | Receptor Binding $K_I$ nM) D2 |
|---|---|---|---|
| 1 | −83 | 21 | 23 |
| 2 | −2 | 0 | 90 |
| 3 | −82 | 20 | 16.3 |
| 4 | −1 | 0 | 280 |

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 50 to about 100 mg of the active ingredient, although other unit dosages may be employed.

In therapeutic use as an antipsychotic agent, the compounds of this invention may be administered in an amount of from about 0.5 to 5 mg/kg per day, and more preferably 1–3 mg/kg per day. The dosages, however may be varied depending upon the requirements of the patient, the severity of the condition being treated, and the compound being employed. Determination of optimum dosages for a particular situation is within the skill of the art.

The following examples describe the invention in greater detail and are intended to illustrate the invention, but not to limit it. In the Examples, the terms $^1$H NMR, CI-MS (chemical ionization mass spectrometry) and IR indicate that the compounds produced were analyzed using such analyses and the results confirmed the structure.

EXAMPLE 1

3-[[3-[[1-[2-(1-Methylethoxy)phenyl]-4-piperazinyl]methyl]phenyl]methyl]-2,4-imidazolidinedione (CP #1)

A solution of α,α-dichoro-m-xylene, 63.76 g (0.364 tool, 3.0 mol-equiv) and triethylamine, 14.73 g (0.146 tool, 1.2 mol-equiv)in 150 mL THF was heated under argon to reflux. N-[2-(1-Methylethoxy)phenyl]-1-piperazine, prepared as described by Martin and Scott, et. al., J. Med. Chem., 1989, 32, 1052–1056, in 150 mL THF was added dropwise over 30 min to the solution. The reaction was maintained at reflux for an additional 90 min. and then allowed to cool to room temperature overnight.

The resulting slurry was filtered and washed with THF. The filtrate was concentrated in vacuo to low volume, diluted with ethyl ether and finally with 3.0N HCl. The resulting slurry was filtered and washed with ethyl ether. The product was dried overnight at room temperature under reduced pressure to afford 31.23 g (67.3%) of 3-[3-[1-[2-(1-methylethoxy)phenyl]-4-piperazinyl]methyl]benzyl chloride hydrochloride.

To a slurry of 300 mg (10.01 mmol, 1.1 mol-equiv) of sodium hydride in 30 mL dimethylformamide under argon was added 1.002 g (10.01 mmol, 1.1 eq.) of hydantoin. The mixture was allowed to stir at room temperature for 30 min. at which time 3-[3-[[1-[2-(1-methylethoxy)phenyl]-4-piperazinyl]methyl]benzyl chloride was added in 10 mL dimethylformamide. The reaction mixture was heated to 70° C. with an oil bath and held for approximately 16 hours.

The reaction mixture was concentrated in vacuo to a residue and partitioned between $CH_2Cl_2$ and $H_2O$. The layers were separated and the aqueous phase was back-extracted with $CH_2Cl_2$. The organic layers were combined, extracted with saturated aqueous NaCl and separated, dried over $MgSO_4$, filtered and finally concentrated in vacuo to a residue.

The residue was purified using chromatography on flash grade silica gel using $MeOH/CH_2Cl_2$ mixture as an eluent. The appropriate fractions were combined and concentrated in vacuo to an oil. The oil was triturated with acetone/hexane and the resulting slurry was filtered. The product was then recrystallized from isopropanol and subsequently dried under reduced pressure at 65° C. to afford 1.889 g (49%) of 3-[[3-[[1-[2-(1-methylethoxy)phenyl]-4-piperazinyl]methyl]phenyl]methyl]-2,4-imidazolidinedione.

Anal. for $C_{24}H_{30}N_4O_3$:

|       | C     | H    | N     |
|-------|-------|------|-------|
| Calc. | 68.22 | 7.16 | 13.26 |
| Found | 68.28 | 7.17 | 13.23 |

$^1$H NMR, Cl mass spec., IR

EXAMPLE 2

1-[[3-[[1-[2-(1-Methylethoxy)phenyl]-4-piperazinyl]methyl]phenyl]methyl]-2,4-imidazolidinedione Dihydrochloride (CP #2)

A mixture of 1.750 g (8.8 mmol, 1.1 eq) 3-(N-morpholinomethyl)-2,4-imidazolidinedione prepared as described in Orazi and Corral, Tetrahedron 1961, 15, 93–99 and 0.264 g (8.8 mmol, 1.1 eq) sodium hydride were combined in 25 mL DMF at room temperature under argon. After $H_2$ evolution had ceased, a solution of 2.87 g (8.0 mmol, 1.0 eq.) 3-[3-[1-[2-(1-methylethoxy)phenyl]-4-piperazinyl]methyl]benzyl chloride hydrochloride, prepared as described in Example 1, in 15 mL DMF was added and the reaction was allowed to stir at room temperature for approximately 16 h. The reaction mixture was then concentrated in vacuo to an oily residue. The residue was combined with 40 mL 3N NaOH under argon and stirred at room temperature for 30 min. The reaction was neutralized with acetic acid, diluted with $CH_2Cl_2$ and $H_2O$ and transferred to a separatory funnel. The layers were separated and the aqueous layer was back-extracted with $CH_2Cl_2$. The organic layers were combined, extracted with sat. aq. NaCl and separated, dried over $MgSO_4$, and then concentrated to a residue.

The crude product was purified by chromatography on flash grade silica gel using an $MeOH/CH_2Cl_2$ mixture as an eluent. The appropriate fractions were combined and concentrated in vacuo to an oil. The oil was dissolved in ethyl ether and added dropwise to a solution of $Et_2O/HCl$. The product was filtered, washed with $Et_2O$ and then dried under reduced pressure for 14 h to afford 0.738 g (18%) of the title compound as a dihydrochloride 0.25 hydrate. mp. 14.4.0°–146° C.

Anal. for $C_{24}H_{30}N_4O_3.2HCl.0.25H_2O$:

$^1$H NMR, Cl mass spec., IR

|       | C     | H    | N     | $H_2O$ |
|-------|-------|------|-------|--------|
| Calc. | 57.66 | 6.55 | 11.21 | 0.90   |
| Found | 57.65 | 6.66 | 11.19 | 2.13   |

EXAMPLE 3

5-[[3-[[1-[2-(1-Methylethoxy)phenyl]-4piperazinyl]methyl]phenyl]methyl]-2,4-imidazolidinedione (CP #3)

Sodium metal, 0.192 g (8.34 mmol, 1.1 eq.), was dissolved in 25 mL dry ethanol at reflux under argon. After dissolution, the alkoxide solution was cooled to room temperature and a solution of 1.649 g (7.59 mmol, 1.0 eq.) diethyl acetamidomalonate was added and the solution was further cooled to 0°–5° C. with an ice/water bath. A solution of 2.725 g (7.59 mmol. 1.0 eq.) 3-[3-[[1-[2-(1-methylethoxy)phenyl]-4-piperazinyl]methyl]benzyl chloride in 12 mL dry ethanol was then added and the reaction was heated to reflux for approximately 3.0 h and then allowed to cool to room temperature.

The resulting slurry was filtered and the filtrate was concentrated in vacuo to a residue and chromatographed on flash grade silica gel using EtOAc/hexane mixture as eluent. The appropriate fractions were combined and concentrated in vacuo to an oil. The purified product was dissolved in $Et_2O$ and added dropwise to a solution of ethereal HCl. The resulting slurry was filtered, washed with $Et_2O$, and the product was dried under reduced pressure at room temperature overnight to provide 2.060 g (43%) of diethyl-2-(acetylamino)-2-[[3-[[1-[2-(1-methylethoxy)phenyl]-4-piperazinyl]methyl]phenyl]methyl]-1,3-propanedioate as a dihydrochloride 1.5 hydrate.

To a mixture of 10.37 g (19.21 mmol, 1.0 mol-equiv) crude diethyl-2-(acetylamino)-2-[[3-[[1-[2-(1-methylethoxy)phenyl]-4-piperazinyl]methyl]phenyl]methyl]-1,3-propanedioate and 40 mL $H_2O$ was cautiously added 10.00 mL (198 mmol, 10.3 eq.) conc. $H_2SO_4$ with agitation. The reaction mixture was heated to reflux and held for 14 h. The solution was then cooled to 0°–5° C. with an ice/water bath and basified by addition of conc. $NH_4OH$. The mixture was diluted with $Et_2O$ and transferred to a separatory funnel. After separating the layers, the aqueous layer was extracted again with $Et_2O$. The aqueous layer was then concentrated in vacuo to a residue and purified by reverse-phase chromatography. The appropriate fractions were concentrated to a residue and triturated with $CH_3CN$. The product was filtered, washed with cold $CH_3CN$, and then dried overnight at 65° C. under reduced pressure to afford 3.055 g (40%) of 2-amino-3-[[3-[[1-[2-(1-methylethoxy)phenyl]-4-piperazinyl]methyl]phenyl]methyl]-1-propionate.

A mixture of 1.800 g (4.53 mmol, 1.0 eq.) 2-amino-3-[[3-[[1-[2-(1-methylethoxy)phenyl]-4-piperazinyl]methyl]phenyl]methyl]-1-propionate and 0.734 g (9.06 mmol, 2.0 mol-equiv) potassium cyanate were combined in 18 mL $H_2O$ and heated at 100° C. for 1.0 h. 34.6 mL (0.83 tool, 92 mol-equiv) of conc. HCl was added as quickly as possible with vigorous agitation and no additional heat. After stirring for approximately 30 min, the reaction mixture was cooled to 0°–5° C. and neutralized by dropwise addition of sat. aq $NaHCO_3$. A small quantity of colored material was filtered from the solution before complete neutralization. The product precipitated directly from the mixture on neutralization and was filtered, washed with water, and dried under vacuum at 6° C. for 24 h to provide 1.805 g (94.3%) of the title compound, m.p. 178°–181° C.

Anal. for $C_{24}H_{30}N_4O_3$:

|  | C | H | N |
|---|---|---|---|
| Calc | 68.22 | 7.16 | 13.26 |
| Found | 68.20 | 7.17 | 13.32 |

$^1$H-NMR, Cl mass spec., IR

EXAMPLE 4

3-[[3-[[1-[2-(methylethoxy)phenyl]-4-piperazinyl]methyl]phenyl]methyl]-imidazolidine-4-one-2-thione (CP #4)

To a solution of 66.50 g (0.352 mol, 1.0 mol-equiv) 3-chloromethylbenzoylchloride in 400 mL $CH_2Cl_2$ at 0°–5° C. under argon was added 47.6 mL (0.704, 2.0 mol-equiv) concentrated aqueous $NH_4OH$ over 25 min. The resulting slurry was filtered, washed with water and the product was dried overnight at 50° C. under vacuum to provide 48.59 g (81%) of 3-chloromethylbenzamide.

A mixture of 15.00 g (88.44 mmol, 1.0 mol-equiv)the benzamide and 8.95 g (106 mmol, 1.2 mol-equiv)triethylamine in 100 mL THF under argon was heated to reflux. A solution of 19.46 g (88.44 mmol, 1.0 mol-equiv) N-[2-(1-methylethoxy)phenyl]-1-piperazine was added dropwise over 30 min. The reaction was maintained for approximately 3.0 hrs and then filtered while still hot. The filtrate was concentrated in vacuo to an oil and then triturated with $CH_2Cl_2$. The resulting slurry was filtered, washed with $CH_2Cl_2$, and the product was dried overnight at room temperature under reduced pressure to provide 24.62 g (79%) of 3-[[1-[2-(1-methylethoxy)phenyl]-4-piperazinyl]-methyl]benzamide.

A slurry of 3.19 g (84.1 mmol, 3.0 mol-equiv) $LiAlH_4$ in 200 mL dioxane was heated to reflux under argon. A slurry of 9.90 g (28.4 mmol, 1.0 mol-equiv) 3-[[1-[2-(1-methylethoxy)phenyl]-4-piperazinyl]methyl]benzamide in 100 mL dioxane was added and the slurry was refluxed for several minutes and then cooled to room temperature. The reaction was then quenched with $H_2O$ and NaOH. The resulting slurry was combined with anhydrous $NaSO_4$, filtered, washed with dioxane and the filtrate was concentrated in vacuo to an oil. The oil was added to ethereal HCl and the precipitated salt was filtered, washed with $Et_2O$, and then dried at room temperature overnight under reduced pressure to provide 14.4 g of the benzyl amine as a hydrochloride salt.

A solution of 1.708 g (5.04 mmol, 1.0 mol-equiv) of the benzyl amine as a free base, 0.882 g (5.04 mmol, 1.0 mol-equiv) BOC-glycine, 1.039 g DCC (5.04 mmol, 1.0 mol-equiv) and 1.361 g (10.1 mmol, 1.0 mol-equiv) hydroxybenzotriazole in 40 mL THF under argon was allowed to stir at room temperature overnight. The reaction was filtered and the filtrate concentrated to an oil and partitioned between $CH_2Cl_2$ and sat. aq. $NaHCO_3$. The layers were separated and the aqueous layer was back-extracted. The combined organics were extracted with sat. aq. NaCl, dried over $MgSO_4$, and then concentrated to an oil: 2.742 g.

The impure N-BOC glycine amide was then dissolved in 15 mL TFA at 0°–5° C. and allowed to react for 1 h under argon. The reaction was neutralized with 3.0N NaOH and extracted with $CH_2Cl_2$. The aqueous layer was back-extracted and then the organic layers were combined, extracted with sat. aq. NaCl, dried over $MgSO_4$ and then concentrated to an oil: 2.118 g.

The crude glycine amide was then dissolved in 30 mL $CH_2Cl_2$ and cooled under argon to 0°–5° C. A solution of 0.394 mL (5.04, 1.0 mol-equiv) thiophosgene in 5 mL $CH_2Cl_2$ was added followed by 0.703 mL triethylamine. The reaction mixture was diluted with sat. aq. $NaHCO_3$ and transferred to a separatory funnel. The layers were separated and the aqueous layer was back-extracted with $CH_2Cl_2$. The organic layers were combined, extracted with sat. aq. NaCl, dried over $MgSO_4$, and then concentrated in vacuo to an oil. The oil was purified by chromatography on silica gel and the appropriate fractions were combined and concentrated to an oil and dissolved in $Et_2O$. The oil was added to ethereal HCl and the resulting slurry was filtered and washed with $Et_2O$. The product was dried under reduced pressure at room temperature to provide 0.814 g (29%) of the title compound as a dihydrochloride salt. m.p. 202°–205° C.

Anal. for $C_{24}H_{30}N_4O_2S.2HCl.0.25H_2O$:

|  | C | H | N | $H_2O$ |
|---|---|---|---|---|
| Calc. | 55.86 | 6.35 | 0.86 | 0.87 |
| Found | 55.90 | 6.21 | 10.57 | 2.64 |

$^1$H NMR, Cl mass spec., IR

We claim:

1. A compound represented by

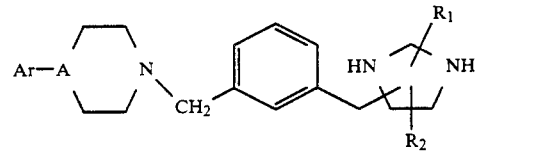

where

A is N;

Ar is aryl or substituted aryl; wherein the substituents for the aryl are selected from any of $C_1$–$C_8$ alkyl, $C_3$–$C_{10}$ cycloalkyl, $C_1$–$C_8$ hydroxyalkyl, $C_1$–$C_6$ alkoxy, aryloxy, hydroxyl, trifluoromethyl, trifluoromethoxy, cyano, $C_1$–$C_8$ alkythio, halogen nitro, $C_1$–$C_8$ haloalkyl, amino or $C_1$–$C_8$ mono- or dialkylamino;

$R_1$ and $R_2$ may be the same or different and are selected from either =O (oxo group) or =S (thioxo group);

or the pharmaceutically acceptable salts thereof.

2. The compound of claim 1, wherein Ar is substituted phenyl.

3. The compound of claim 2, wherein the substituent is $C_1$–$C_8$ alkoxy.

4. The compound of claim 3, wherein the substituent is isopropoxy.

5. The compound of claim 4, wherein the substituent is substituted in the 2 position on the phenyl ring.

6. The compound of claim 1, wherein at least one of $R_1$ and $R_2$ is O.

7. The compound of claim 1, wherein the imidazolidine ring is attached to the remainder of the molecule at one of the ring nitrogen atoms.

8. The compound of claim 1, wherein the imidazolidine ring is attached to one of the ring carbon atoms.

9. The compound of claim 1, having the name 3-[[3-[[1-[2-(1-methylethoxy)phenyl]-4-piperazinyl]methyl]phenyl]methyl]-2,4-imidazolidinedione.

10. The compound of claim 1, having the name 1-[[3-[[1-[2-(1-methylethoxy)phenyl]-4-piperazinyl]methyl]phenyl]methyl]-2, 4-imidazolidinedione.

11. The compound of claim 1 having the name 5-[[3-[[1-[2-(1-methylethoxy)phenyl]-4-piperazinyl]methyl]phenyl]methyl]-2,4-imidazolidinedione.

12. The compound of claim 1 having the name 3-[[3-[[1-[2-(methylethoxy)phenyl]-4-piperazinyl]methyl]phenyl]methyl]-imidazolidine-4-one-2-thione.

13. A composition for treating psychotic conditions in mammals comprising the compound of claim 1 and a pharmaceutically acceptable carrier, said compound being present in a therapeutically effective amount for treating psychotic conditions in mammals.

14. A method for treating psychotic conditions in mammals comprising administering to a mammal in need of such treatment the compound of claim 1 in an amount sufficient to treat such conditions.

15. The method of claim 14, wherein the condition is schizophrenia.

16. The method of claim 14, wherein the effective amount is about 0.5 to 5 mg/kg per day.

* * * * *